United States Patent [19]
Hofmann et al.

[11] Patent Number: 5,840,306
[45] Date of Patent: Nov. 24, 1998

[54] DNA ENCODING HUMAN PAPILLOMAVIRUS TYPE 18

[75] Inventors: Kathryn J. Hofmann, Collegeville; Kathrin U. Jansen, Ft. Washington; Michael P. Neeper, Collegeville, all of Pa.

[73] Assignee: Merck & Co., Inc., Rahway, N.J.

[21] Appl. No.: 408,669

[22] Filed: Mar. 22, 1995

[51] Int. Cl.⁶ .......................... A61K 39/12; C07H 21/04; C12N 5/10; C12N 15/86
[52] U.S. Cl. .................................. 424/186.1; 424/204.1; 514/44; 435/254.21; 435/320.1; 435/348; 435/365; 536/23.72
[58] Field of Search ................................. 435/69.1, 172.1, 435/172.3, 320.1, 69.3, 348, 365, 254.21; 536/23.1, 23.72; 424/204.1, 93.1, 93.2, 93.6, 186.1; 514/44

[56] References Cited

U.S. PATENT DOCUMENTS 5,437,951   8/1995   Lowy et al. .

FOREIGN PATENT DOCUMENTS

WO 93/02184   4/1993   WIPO .
WO 94 00152   1/1994   WIPO .
WO 94/05792   3/1994   WIPO .
WO 94/20137   9/1994   WIPO .

OTHER PUBLICATIONS

Kaufman, Methods in Enzymology, vol. 185, pp. 487–511, 1990.
Cole, et al., "Nucleotide Sequence and Comparative Analysis of the Human Papillomavius Type 18 Genome", J. Mol. Biol., 193 (4), pp. 599–608 (1987).
Browne, et al., "Analysis of the L1 Gene Product of Human Papillomavirus Type 16 by Expression in a Vaccinia Virus Recombinant" J. Gen. Virol. (1988) vol. 69, pp. 1263–1273.
Doorbar, et al., "Identification of Proteins Encoded by the L1 and L2 Open Reading Frames of Human Papillomavirus 1a", J. of Virol., Sep. 1987, vol. 67, No. 9., pp. 2793–2799.

Hanenese, et al., "Self–Assembly of Human Papillomavirus Type 1 Capsids by Expression of the L2 Protein Alone or by Coexpression . . . ", J. of Virol., Jan. 1993, vol. 67, No. 1, pp. 315–322.
Kirnbauer, R., "Papillomavirus L1 Major Capsid Protein Self–assembles into Virus–like Particles that are Highly Immunogenic", Proc. Natl. Acad. Sci., vol. 89, pp. 12180–12184, Dec. 1992.
LeCann, et al., "Self–Assembly of Human Papillomavirus Type 16 Capsids by Expression of the L1 Protein in Insect Cells", FEMS Microb. Lett., 117 (1994), pp. 269–274.
Lin, et al., "Effective Vaccination Against Papilloma Development by Immunication with L1 or L2 Structural Protein . . . ", Virology, vol. 187, (1992) pp. 612–619.
Rose, et al., "Expression of Human Papillomavirus Type 11 L1 Protein in Insect Cells: In Vivo and In Vitro Assembly of Viruslike Particles", J. of Virol., Apr. 1993, pp. 1936–1944.
Steele, et al., "Humoral Assays of Human Sera to Disrupted and Nondisrupted Epitopes of Human Papillomavirus Type 1", Virology, vol. 174, (1990) pp. 388–398.
Strike, et al., "Expression in *Escherichia Coli* of Seven DNA Fragments Comprising the Complete L1 and L2 Open . . . ", J. Gen. Virol. (1989) vol. 70, pp. 543–555.
Zhou, et al., "Synthesis and Assembly of Infectious Bovine Papillomavirus Particles In Bitro", J. Gen. Virol., (1993), Fol. 74, pp. 763–768.
Zhou, et al., "Expression of Vaccinia Recombinant HPV HPV 16 L1 and L2 ORF Proteins in Eipthelial Cells . . . ", Virology, vol. 185, (1991), pp. 251–257.
Zhou, et al., "Increased Antibody Responses to Human Papillomavirus Type 16 L1 Protein Expressed by Recombinant Vaccinia . . . ", J. Gen. Virology, (1990), vol. 71, pp. 2185–2190.
Sasagawa et al., "Synthesis and Assembly of Virus–like Particles of Human Papillomaviruses Type 6 . . . ", Virology, 206, pp. 126–135 (1995).

*Primary Examiner*—David Guzo
*Attorney, Agent, or Firm*—Joanne M. Giesser; Jack L. Tribble

[57] ABSTRACT

The present invention is directed to DNA molecules encoding purified human papillomavirus type 18 and derivatives thereof.

13 Claims, 7 Drawing Sheets

```
            10        20        30        40        50        60
      ATGGCTTTGTGGCGGCCTAGTGACAATACCGTATACCTTCCACCTCCTTCTGTGGCAAGA
  1   M  A  L  W  R  P  S  D  N  T  V  Y  L  P  P  P  S  V  A  R    20
            70        80        90        100       110       120
      GTTGTAAATACTGATGATTATGTGACTCGCACAAGCATATTTTATCATGCTGGCAGCTCT
 21   V  V  N  T  D  D  Y  V  T  R  T  S  I  F  Y  H  A  G  S  S    40
            130       140       150       160       170       180
      AGATTATTAACTGTTGGTAATCCATATTTTAGGGTTCCTGCAGGTGGTGGCAATAAGCAG
 41   R  L  L  T  V  G  N  P  Y  F  R  V  P  A  G  G  G  N  K  Q    60
            190       200       210       220       230       240
      GATATTCCTAAGGTTTCTGCATACCAATATAGAGTATTTCGGGTGCAGTTACCTGACCCA
 61   D  I  P  K  V  S  A  Y  Q  Y  R  V  F  R  V  Q  L  P  D  P    80
            250       260       270       280       290       300
      AATAAATTTGGTTTACCTGATAATAGTATTTATAATCCTGAAACACAACGTTTAGTGTGG
 81   N  K  F  G  L  P  D  N  S  I  Y  N  P  E  T  Q  R  L  V  W   100
            310       320       330       340       350       360
      GCCTGTGCTGGAGTGGAAATTGGCCGTGGTCAGCCTTTAGGTGTTGGCCTTAGTGGGCAT
101   A  C  A  G  V  E  I  G  R  G  Q  P  L  G  V  G  L  S  G  H   120
            370       380       390       400       410       420
      CCATTTTATAATAAATTAGATGACACTGAAAGTTCCCATGCCGCTACGTCTAATGTTTCT
121   P  F  Y  N  K  L  D  D  T  E  S  S  H  A  A  T  S  N  V  S   140
            430       440       450       460       470       480
      GAGGACGTTAGGGACAATGTGTCTGTAGATTATAAGCAGACACAGTTATGTATTTTGGGC
141   E  D  V  R  D  N  V  S  V  D  Y  K  Q  T  Q  L  C  I  L  G   160
            490       500       510       520       530       540
      TGTGCCCCTGCTATTGGGGAACACTGGGCTAAAGGCACTGCTTGTAAATCGCGTCCTTTA
161   C  A  P  A  I  G  E  H  W  A  K  G  T  A  C  K  S  R  P  L   180
            550       560       570       580       590       600
      TCACAGGGCGATTGCCCCCCTTTAGAACTTAAGAACACAGTTTTGGAAGATGGTGATATG
181   S  Q  G  D  C  P  P  L  E  L  K  N  T  V  L  E  D  G  D  M   200
            610       620       630       640       650       660
      GTAGATACTGGATATGGTGCCATGGACTTTAGTACATTGCAAGATACTAAATGTGAGGTA
201   V  D  T  G  Y  G  A  M  D  F  S  T  L  Q  D  T  K  C  E  V   220
            670       680       690       700       710       720
      CCATTGGATATTTGTCAGTCTATTTGTAAATATCCTGATTATTTACAAATGTCTGCAGAT
221   P  L  D  I  C  Q  S  I  C  K  Y  P  D  Y  L  Q  M  S  A  D   240
            730       740       750       760       770       780
      CCTTATGGGGATTCCATGTTTTTTTGCTTACGACGTGAGCAGCTTTTTGCTAGGCATTTT
241   P  Y  G  D  S  M  F  F  C  L  R  R  E  Q  L  F  A  R  H  F   260
            790       800       810       820       830       840
      TGGAATAGGGCAGGTACTATGGGTGACACTGTGCCTCAATCCTTATATATTAAAGGCACA
261   W  N  R  A  G  T  M  G  D  T  V  P  Q  S  L  Y  I  K  G  T   280
```

FIG. 1A

```
                850       860       870       880       890       900
          GGTATGCGTGCTTCACCTGGCAGCTGTGTGTATTCTCCCTCTCCAAGTGGCTCTATTGTT
      281  G  M  R  A  S  P  G  S  C  V  Y  S  P  S  P  S  G  S  I  V   300
                910       920       930       940       950       960
          ACCTCTGACTCCCAGTTGTTTAATAAACCATATTGGTTACATAAGGCACAGGGTCATAAC
      301  T  S  D  S  Q  L  F  N  K  P  Y  W  L  H  K  A  Q  G  H  N   320
                970       980       990      1000      1010      1020
          AATGGTATCTGCTGGCATAATCAATTATTTGTTACTGTGGTAGATACCACTCGTAGTACC
      321  N  G  I  C  W  H  N  Q  L  F  V  T  V  V  D  T  T  R  S  T   340
               1030      1040      1050      1060      1070      1080
          AATTTAACAATATGTGCTTCTACACAGTCTCCTGTACCTGGGCAATATGATGCTACCAAA
      341  N  L  T  I  C  A  S  T  Q  S  P  V  P  G  Q  Y  D  A  T  K   360
               1090      1100      1110      1120      1130      1140
          TTTAAGCAGTATAGCAGACATGTTGAAGAATATGATTTGCAGTTTATTTTTCAGTTATGT
      361  F  K  Q  Y  S  R  H  V  E  E  Y  D  L  Q  F  I  F  Q  L  C   380
               1150      1160      1170      1180      1190      1200
          ACTATTACTTTAACTGCAGATGTTATGTCCTATATTCATAGTATGAATAGCAGTATTTTA
      381  T  I  T  L  T  A  D  V  M  S  Y  I  H  S  M  N  S  S  I  L   400
               1210      1220      1230      1240      1250      1260
          GAGGATTGGAACTTTGGTGTTCCCCCCCCGCCAACTACTAGTTTGGTGGATACATATCGT
      401  E  D  W  N  F  G  V  P  P  P  P  T  T  S  L  V  D  T  Y  R   420
               1270      1280      1290      1300      1310      1320
          TTTGTACAATCTGTTGCTATTACCTGTCAAAAGGATGCTGCACCAGCTGAAAATAAGGAT
      421  F  V  Q  S  V  A  I  T  C  Q  K  D  A  A  P  A  E  N  K  D   440
               1330      1340      1350      1360      1370      1380
          CCCTATGATAAGTTAAAGTTTTGGAATGTGGATTTAAAGGAAAAGTTTTCTTTGGACTTA
      441  P  Y  D  K  L  K  F  W  N  V  D  L  K  E  K  F  S  L  D  L   460
               1390      1400      1410      1420      1430      1440
          GATCAATATCCCCTTGGACGTAAATTTTTGGTTCAGGCTGGATTGCGTCGCAAGCCCACC
      461  D  Q  Y  P  L  G  R  K  F  L  V  Q  A  G  L  R  R  K  P  T   480
               1450      1460      1470      1480      1490      1500
          ATAGGCCCTCGTAAACGTTCTGCTCCATCTGCCACTACGTCTTCTAAACCTGCCAAGCGT
      481  I  G  P  R  K  R  S  A  P  S  A  T  T  S  S  K  P  A  K  R   500
               1510      1520
          GTGCGTGTACGTGCCAGGAAGTAA
      501  V  R  V  R  A  R  K  *                                       508
```

FIG. 1B

AMINO ACID VARIATIONS IN L1 PROTEIN OF HPV18

AMINO ACID POSITION IN L1

| | 30 | 88 | 283 | 323 | 338 |
|---|---|---|---|---|---|
| HPV18 PUBLISHED | P | T | P | V | P |
| HPV18 MERCK | R | N | R | I | R |
| #354 (CLINICAL INDIANA) | R | N | R | V | R |
| #556 | — | — | R | V | R |
| #755 | — | — | R | V | R |
| #697 | — | — | R | V | R |
| #795 | — | — | R | V | R |
| #23 (CLINICAL PENNSYLVANIA) | — | — | R | I | R |

FIG.2

```
              10         20         30         40         50         60
        ATGGTATCCCACCGTGCCGCACGACGCAAACGGGCTTCGGTGACTGACTTATATAAAACA
      1  M  V  S  H  R  A  A  R  R  K  R  A  S  V  T  D  L  Y  K  T    20
              70         80         90        100        110        120
        TGTAAACAATCTGGTACATGTCCATCTGATGTTGTTAATAAGGTAGAGGGCACCACGTTA
     21  C  K  Q  S  G  T  C  P  S  D  V  V  N  K  V  E  G  T  T  L    40
             130        140        150        160        170        180
        GCAGATAAAATATTGCAATGGTCAAGCCTTGGTATATTTTTGGGTGGACTTGGCATAGGT
     41  A  D  K  I  L  Q  W  S  S  L  G  I  F  L  G  G  L  G  I  G    60
             190        200        210        220        230        240
        ACTGGAAGTGGTACAGGGGGTCGTACAGGGTACATTCCATTGGGTGGGCGTTCCAATACA
     61  T  G  S  G  T  G  G  R  T  G  Y  I  P  L  G  G  R  S  N  T    80
             250        260        270        280        290        300
        GTTGTGGATGTCGGTCCTACACGTCCTCCAGTGGTTATTGAACCTGTGGGCCCCACAGAC
     81  V  V  D  V  G  P  T  R  P  P  V  V  I  E  P  V  G  P  T  D   100
             310        320        330        340        350        360
        CCATCTATTGTTACATTAATAGAGGACTCAAGTGTTGTTACATCAGGTGCACCTAGGCCT
    101  P  S  I  V  T  L  I  E  D  S  S  V  V  T  S  G  A  P  R  P   120
             370        380        390        400        410        420
        ACTTTTACTGGCACGTCTGGGTTTGATATAACATCTGCTGGTACAACTACACCTGCAGTT
    121  T  F  T  G  T  S  G  F  D  I  T  S  A  G  T  T  T  P  A  V   140
             430        440        450        460        470        480
        TTGGATATCACACCTTCGTCTACCTCTGTTTCTATTTCCACAACCAATTTTACCAATCCT
    141  L  D  I  T  P  S  S  T  S  V  S  I  S  T  T  N  F  T  N  P   160
             490        500        510        520        530        540
        GCATTTTCTGATCCGTCCATTATTGAAGTTCCACAAACTGGGGAGGTGTCAGGTAATGTA
    161  A  F  S  D  P  S  I  I  E  V  P  Q  T  G  E  V  S  G  N  V   180
             550        560        570        580        590        600
        TTTGTTGGTACCCCTACATCTGGAACACATGGGTATGAAGAAATACCTTTACAAACATTT
    181  F  V  G  T  P  T  S  G  T  H  G  Y  E  E  I  P  L  Q  T  F   200
             610        620        630        640        650        660
        GCTTCTTCTGGTACGGGGGAGGAACCCATTAGTAGTACCCCATTGCCTACTGTGCGGCGT
    201  A  S  S  G  T  G  E  E  P  I  S  S  T  P  L  P  T  V  R  R   220
             670        680        690        700        710        720
        GTAGCAGGTCCCCGCCTTTACAGTAGGGCCTACCAACAAGTGTCTGTGGCTAACCCTGAG
    221  V  A  G  P  R  L  Y  S  R  A  Y  Q  Q  V  S  V  A  N  P  E   240
             730        740        750        760        770        780
        TTTCTTACACGTCCATCCTCTTTAATTACCTATGACAACCCGGCCTTTGAGCCTGTGGAC
    241  F  L  T  R  P  S  S  L  I  T  Y  D  N  P  A  F  E  P  V  D   260
             790        800        810        820        830        840
        ACTACATTAACATTTGAGCCTCGTAGTAATGTTCCTGATTCAGATTTTATGGATATTATC
    261  T  T  L  T  F  E  P  R  S  N  V  P  D  S  D  F  M  D  I  I   280
```

FIG. 3A

```
                    850        860        870        880        890        900
         CGTTTACATAGGCCTGCTTTAACATCCAGGCGTGGTACTGTGCGCTTTAGTAGATTAGGT
    281  R  L  H  R  P  A  L  T  S  R  R  G  T  V  R  F  S  R  L         300
                    910        920        930        940        950        960
         CAAAGGGCAACTATGTTTACCCGTAGCGGTACACAAATAGGTGCTAGGGTTCACTTTTAT
    301  Q  R  A  T  M  F  T  R  S  G  T  Q  I  G  A  R  V  H  F  Y      320
                    970        980        990       1000       1010       1020
         CATGATATAAGTCCTATTGCACCCTCCCCAGAATATATTGAACTGCAGCCTTTAGTATCT
    321  H  D  I  S  P  I  A  P  S  P  E  Y  I  E  L  Q  P  L  V  S      340
                   1030       1040       1050       1060       1070       1080
         GCCACGGAGGACAATGGCTTGTTTGATATATATGCAGATGACATAGACCCTGCAATGCCT
    341  A  T  E  D  N  G  L  F  D  I  Y  A  D  D  I  D  P  A  M  P      360
                   1090       1100       1110       1020       1030       1040
         GTACCATCGCGTCCTACTACCTCCTCTGCAGTTTCTACATATTCGCCCACTATATCATCT
    361  V  P  S  R  P  T  T  S  S  A  V  S  T  Y  S  P  T  I  S  S      380
                   1150       1160       1170       1180       1190       1200
         GCCTCTTCCTATAGTAATGTAACGGTCCCTTTAACCTCCTCTTGGGATGTGCCTGTATAC
    381  A  S  S  Y  S  N  V  T  V  P  L  T  S  S  W  D  V  P  V  Y      400
                   1210       1220       1230       1240       1250       1260
         ACGGGTCCTGATATTACATTACCACCTACTACCTCTGTATGGCCCATTGTATCACCCACA
    401  T  G  P  D  I  T  L  P  P  T  T  S  V  W  P  I  V  S  P  T      420
                   1270       1280       1290       1300       1310       1320
         GCCCCTGCCTCTACACAGTATATTGGTATACATGGTACACATTATTATTTGTGGCCATTA
    421  A  P  A  S  T  Q  Y  I  G  I  H  G  T  H  Y  Y  L  W  P  L      440
                   1330       1340       1350       1360       1370       1380
         TATTATTTTATTCCTAAAAAGCGTAAACGTGTTCCCTATTTTTTTGCAGATGGCTTTGTG
    441  Y  Y  F  I  P  K  K  R  K  R  V  P  Y  F  F  A  D  G  F  V      460

GCGGCCTAG
    461  A  A  *                                                          463
```

FIG. 3B

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 1524 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
ATGGCTTTGT    GGCGGCCTAG    TGACAATACC    GTATACCTTC    CACCTCCTTC    TGTGGCAAGA      60

GTTGTAAATA    CTGATGATTA    TGTGACTCGC    ACAAGCATAT    TTTATCATGC    TGGCAGCTCT     120

AGATTATTAA    CTGTTGGTAA    TCCATATTTT    AGGGTTCCTG    CAGGTGGTGG    CAATAAGCAG     180

GATATTCCTA    AGGTTTCTGC    ATACCAATAT    AGAGTATTTC    GGGTGCAGTT    ACCTGACCCA     240

AATAAATTTG    GTTTACCTGA    TAATAGTATT    TATAATCCTG    AAACACAACG    TTTAGTGTGG     300

GCCTGTGCTG    GAGTGGAAAT    TGGCCGTGGT    CAGCCTTTAG    GTGTTGGCCT    TAGTGGGCAT     360

CCATTTTATA    ATAAATTAGA    TGACACTGAA    AGTTCCCATG    CCGCTACGTC    TAATGTTTCT     420

GAGGACGTTA    GGGACAATGT    GTCTGTAGAT    TATAAGCAGA    CACAGTTATG    TATTTTGGGC     480
```

| | | | | | |
|---|---|---|---|---|---|
| TGTGCCCCTG | CTATTGGGGA | ACACTGGGCT | AAAGGCACTG | CTTGTAAATC | GCGTCCTTTA | 540
| TCACAGGGCG | ATTGCCCCCC | TTTAGAACTT | AAGAACACAG | TTTTGGAAGA | TGGTGATATG | 600
| GTAGATACTG | GATATGGTGC | CATGGACTTT | AGTACATTGC | AAGATACTAA | ATGTGAGGTA | 660
| CCATTGGATA | TTTGTCAGTC | TATTTGTAAA | TATCCTGATT | ATTTACAAAT | GTCTGCAGAT | 720
| CCTTATGGGG | ATTCCATGTT | TTTTGCTTA | CGACGTGAGC | AGCTTTTGC | TAGGCATTTT | 780
| TGGAATAGGG | CAGGTACTAT | GGGTGACACT | GTGCCTCAAT | CCTTATATAT | TAAAGGCACA | 840
| GGTATGCGTG | CTTCACCTGG | CAGCTGTGTG | TATTCTCCCT | CTCCAAGTGG | CTCTATTGTT | 900
| ACCTCTGACT | CCCAGTTGTT | TAATAAACCA | TATTGGTTAC | ATAAGGCACA | GGGTCATAAC | 960
| AATGGTATCT | GCTGGCATAA | TCAATTATTT | GTTACTGTGG | TAGATACCAC | TCGTAGTACC | 1020
| AATTTAACAA | TATGTGCTTC | TACACAGTCT | CCTGTACCTG | GGCAATATGA | TGCTACCAAA | 1080
| TTTAAGCAGT | ATAGCAGACA | TGTTGAAGAA | TATGATTTGC | AGTTTATTTT | TCAGTTATGT | 1140
| ACTATTACTT | TAACTGCAGA | TGTTATGTCC | TATATTCATA | GTATGAATAG | CAGTATTTTA | 1200
| GAGGATTGGA | ACTTTGGTGT | TCCCCCCCCG | CCAACTACTA | GTTGGTGGA | TACATATCGT | 1260
| TTTGTACAAT | CTGTTGCTAT | TACCTGTCAA | AAGGATGCTG | CACCAGCTGA | AAATAAGGAT | 1320
| CCCTATGATA | AGTTAAAGTT | TTGGAATGTG | GATTTAAAGG | AAAAGTTTTC | TTTGGACTTA | 1380
| GATCAATATC | CCCTTGGACG | TAAATTTTTG | GTTCAGGCTG | GATTGCGTCG | CAAGCCCACC | 1440
| ATAGGCCCTC | GTAAACGTTC | TGCTCCATCT | GCCACTACGT | CTTCTAAACC | TGCCAAGCGT | 1500
| GTGCGTGTAC | GTGCCAGGAA | GTAA | | | | 1524

( 2 ) INFORMATION FOR SEQ ID NO:2:

( i ) SEQUENCE CHARACTERISTICS:
        ( A ) LENGTH: 507 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Met Ala Leu Trp Arg Pro Ser Asp Asn Thr Val Tyr Leu Pro Pro Pro
 1               5                  10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
        35                  40                  45

Tyr Phe Arg Val Pro Ala Gly Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Asn Ser Ile Tyr Asn Pro Glu Thr Gln
                85                  90                  95

Arg Leu Val Trp Ala Cys Ala Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125
```

Thr Glu Ser Ser His Ala Ala Thr Ser Asn Val Ser Glu Asp Val Arg
130                     135                 140

Asp Asn Val Ser Val Asp Tyr Lys Gln Thr Gln Leu Cys Ile Leu Gly
145                 150                 155                     160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190

Thr Val Leu Glu Asp Gly Asp Met Val Asp Thr Gly Tyr Gly Ala Met
            195                 200                 205

Asp Phe Ser Thr Leu Gln Asp Thr Lys Cys Glu Val Pro Leu Asp Ile
    210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
        275                 280                 285

Cys Val Tyr Ser Pro Ser Ser Gly Ser Ile Val Thr Ser Asp Ser
    290                 295                 300

Gln Leu Phe Asn Lys Pro Tyr Trp Leu His Lys Ala Gln Gly His Asn
305                 310                 315                 320

Asn Gly Ile Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Thr Thr Ser Leu Val
                405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
        435                 440                 445

Asn Val Asp Leu Lys Glu Lys Phe Ser Leu Asp Leu Asp Gln Tyr Pro
450                 455                 460

Leu Gly Arg Lys Phe Leu Val Gln Ala Gly Leu Arg Arg Lys Pro Thr
465                 470                 475                 480

Ile Gly Pro Arg Lys Arg Ser Ala Pro Ser Ala Thr Thr Ser Ser Lys
                485                 490                 495

Pro Ala Lys Arg Val Arg Val Arg Ala Arg Lys
                500                 505

( 2 ) INFORMATION FOR SEQ ID NO:3:

( i ) SEQUENCE CHARACTERISTICS:
        ( A ) LENGTH: 1389 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

| | | | | | | |
|---|---|---|---|---|---|---|
| ATGGTATCCC | ACCGTGCCGC | ACGACGCAAA | CGGGCTTCGG | TGACTGACTT | ATATAAAACA | 60 |
| TGTAAACAAT | CTGGTACATG | TCCATCTGAT | GTTGTTAATA | AGGTAGAGGG | CACCACGTTA | 120 |
| GCAGATAAAA | TATTGCAATG | GTCAAGCCTT | GGTATATTTT | TGGGTGGACT | TGGCATAGGT | 180 |
| ACTGGAAGTG | GTACAGGGGG | TCGTACAGGG | TACATTCCAT | GGGTGGGCG | TTCCAATACA | 240 |
| GTTGTGGATG | TCGGTCCTAC | ACGTCCTCCA | GTGGTTATTG | AACCTGTGGG | CCCCACAGAC | 300 |
| CCATCTATTG | TTACATTAAT | AGAGGACTCA | AGTGTTGTTA | CATCAGGTGC | ACCTAGGCCT | 360 |
| ACTTTTACTG | GCACGTCTGG | GTTTGATATA | ACATCTGCTG | GTACAACTAC | ACCTGCAGTT | 420 |
| TTGGATATCA | CACCTTCGTC | TACCTCTGTT | TCTATTTCCA | CAACCAATTT | TACCAATCCT | 480 |
| GCATTTTCTG | ATCCGTCCAT | TATTGAAGTT | CCACAAACTG | GGGAGGTGTC | AGGTAATGTA | 540 |
| TTTGTTGGTA | CCCCTACATC | TGGAACACAT | GGGTATGAAG | AAATACCTTT | ACAAACATTT | 600 |
| GCTTCTTCTG | GTACGGGGGA | GGAACCCATT | AGTAGTACCC | CATTGCCTAC | TGTGCGGCGT | 660 |
| GTAGCAGGTC | CCCGCCTTTA | CAGTAGGGCC | TACCAACAAG | TGTCTGTGGC | TAACCCTGAG | 720 |
| TTTCTTACAC | GTCCATCCTC | TTTAATTACC | TATGACAACC | CGGCCTTTGA | GCCTGTGGAC | 780 |
| ACTACATTAA | CATTTGAGCC | TCGTAGTAAT | GTTCCTGATT | CAGATTTTAT | GGATATTATC | 840 |
| CGTTTACATA | GGCCTGCTTT | AACATCCAGG | CGTGGTACTG | TGCGCTTTAG | TAGATTAGGT | 900 |
| CAAAGGGCAA | CTATGTTTAC | CCGTAGCGGT | ACACAAATAG | GTGCTAGGGT | TCACTTTTAT | 960 |
| CATGATATAA | GTCCTATTGC | ACCCTCCCCA | GAATATATTG | AACTGCAGCC | TTTAGTATCT | 1020 |
| GCCACGGAGG | ACAATGGCTT | GTTTGATATA | TATGCAGATG | ACATAGACCC | TGCAATGCCT | 1080 |
| GTACCATCGC | GTCCTACTAC | CTCCTCTGCA | GTTTCTACAT | ATTCGCCCAC | TATATCATCT | 1140 |
| GCCTCTTCCT | ATAGTAATGT | AACGGTCCCT | TTAACCTCCT | CTTGGGATGT | GCCTGTATAC | 1200 |
| ACGGGTCCTG | ATATTACATT | ACCACCTACT | ACCTCTGTAT | GGCCCATTGT | ATCACCCACA | 1260 |
| GCCCCTGCCT | CTACACAGTA | TATTGGTATA | CATGGTACAC | ATTATTATTT | GTGGCCATTA | 1320 |
| TATTATTTTA | TTCCTAAAAA | GCGTAAACGT | GTTCCCTATT | TTTTTGCAGA | TGGCTTTGTG | 1380 |
| GCGGCCTAG | | | | | | 1389 |

( 2 ) INFORMATION FOR SEQ ID NO:4:

( i ) SEQUENCE CHARACTERISTICS:
        ( A ) LENGTH: 461 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:4:

```
Met Val Ser His Arg Ala Ala Arg Arg Lys Arg Ala Ser Val Thr Asp
 1               5                  10                  15
Leu Tyr Lys Thr Cys Lys Gln Ser Gly Thr Cys Pro Ser Asp Val Val
                20                  25                  30
Asn Lys Val Glu Gly Thr Thr Leu Ala Asp Lys Ile Leu Gln Trp Ser
            35                  40                  45
Ser Leu Gly Ile Phe Leu Gly Leu Gly Ile Gly Thr Gly Ser Gly
    50                  55                  60
Thr Gly Gly Arg Thr Gly Tyr Ile Pro Leu Gly Gly Arg Ser Asn Thr
65                      70                  75                  80
Val Val Asp Val Gly Pro Thr Arg Pro Pro Val Val Ile Glu Pro Val
                    85                  90                      95
Gly Pro Thr Asp Pro Ser Ile Val Thr Leu Ile Glu Asp Ser Ser Val
            100                 105                 110
Val Thr Ser Gly Ala Pro Arg Pro Thr Phe Thr Gly Thr Ser Gly Phe
        115                 120                 125
Asp Ile Thr Ser Ala Gly Thr Thr Pro Ala Val Leu Asp Ile Thr
    130                 135                 140
Pro Ser Ser Thr Ser Val Ser Ile Ser Thr Thr Asn Phe Thr Asn Pro
145                 150                 155                 160
Ala Phe Ser Asp Pro Ser Ile Ile Glu Val Pro Gln Thr Gly Glu Val
                165                 170                 175
Ser Gly Asn Val Phe Val Gly Thr Pro Thr Ser Gly Thr His Gly Tyr
            180                 185                 190
Glu Glu Ile Pro Leu Gln Thr Phe Ala Ser Ser Gly Thr Gly Glu Glu
        195                 200                 205
Pro Ile Ser Ser Thr Pro Leu Pro Thr Val Arg Arg Val Ala Gly Pro
    210                 215                 220
Arg Leu Tyr Ser Arg Ala Tyr Gln Gln Val Ser Val Ala Asn Pro Glu
225                 230                 235                 240
Phe Leu Thr Arg Pro Ser Ser Leu Ile Thr Tyr Asp Asn Pro Ala Phe
                245                 250                 255
Glu Pro Val Asp Thr Thr Leu Thr Phe Glu Pro Arg Ser Asn Val Pro
            260                 265                 270
Asp Ser Asp Phe Met Asp Ile Ile Arg Leu His Arg Pro Ala Leu Thr
        275                 280                 285
Ser Arg Arg Gly Thr Val Arg Phe Ser Arg Leu Gly Gln Arg Ala Thr
    290                 295                 300
Met Phe Thr Arg Ser Gly Thr Gln Ile Gly Ala Arg Val His Phe Tyr
305                 310                 315                 320
His Asp Ile Ser Pro Ile Ala Pro Ser Pro Glu Tyr Ile Glu Leu Gln
                325                 330                 335
Pro Leu Val Ser Ala Thr Glu Asp Asn Gly Leu Phe Asp Ile Tyr Ala
            340                 345                 350
Asp Asp Ile Asp Pro Ala Met Pro Val Pro Ser Arg Pro Thr Thr Ser
        355                 360                 365
Ser Ala Val Ser Thr Tyr Ser Pro Thr Ile Ser Ser Ala Ser Ser Tyr
    370                 375                 380
Ser Asn Val Thr Val Pro Leu Thr Ser Ser Trp Asp Val Pro Val Tyr
385                 390                 395                 400
Thr Gly Pro Asp Ile Thr Leu Pro Pro Thr Ser Val Trp Pro Ile Val
                405                 410                 415
```

```
Ser  Pro  Thr  Ala  Pro  Ala  Ser  Thr  Gln  Tyr  Ile  Gly  Ile  His  Gly  Thr
               420            425                           430

His  Tyr  Tyr  Leu  Trp  Pro  Leu  Tyr  Tyr  Phe  Ile  Pro  Lys  Lys  Arg  Lys
          435                      440                      445

Arg  Val  Pro  Tyr  Phe  Phe  Ala  Asp  Gly  Phe  Val  Ala  Ala
     450                 455                      460
```

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

GAAGATCTCA CAAAACAAAA TGGCTTTGTG GCGGCCTAGT G      41

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

GAAGATCTTT ACTTCCTGGC ACGTACACGC ACACGC      36

( 2 ) INFORMATION FOR SEQ ID NO:7:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:7:

TCCCCCGGGC ACAAAACAAA ATGGTATCCC ACCGTGCCGC ACGAC      45

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:8:

TCCCCCGGGC TAGGCCGCCA CAAAGCCATC TGC　　　　33

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:9:

CAATCCTTAT ATATTAAAGG CACAGGTATG　　　　30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:10:

CATCATATTG CCCAGGTACA GGAGACTGTG　　　　30

( 2 ) INFORMATION FOR SEQ ID NO:11:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

GAAGATCTCA CAAAACAAAA TGGCTTTGTG GCGGCCTAGT G  41

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

CCTAACGTCC TCAGAAACAT TAGAC  25

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

CTTAAAGCTT ATGTCACTTT CTCTTGTATC  30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

TGATAAGCTT GCTCAATGGT TCTCTTCCTC  30

-continued (2) INFORMATION FOR SEQ ID NO:15:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:15:

TGGTCATCCC AAATCTTGAA A  21

(2) INFORMATION FOR SEQ ID NO:16:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:16:

CACCGTAGTG TTTGGAAGCG A  21

DNA ENCODING HUMAN PAPILLOMAVIRUS TYPE 18

FIELD OF THE INVENTION

The present invention is directed to DNA molecules encoding purified human papillomavirus type 18 and derivatives thereof.

BRIEF DESCRIPTION OF THE DRAWINGS

FIG. 1 shows the HPV 18 L1 nucleotide (SEQ ID NO:1) and deduced amino acid (SEQ ID NO:2) sequences.

FIG. 2 is a list of amino acid variations within the L1 protein of HPV 18.

FIG. 3 shows the HPV 18 L2 nucleotide (SEQ ID NO:3) and deduced amino acid (SEQ ID NO:4) sequences.

BACKGROUND OF THE INVENTION

Figure 4:
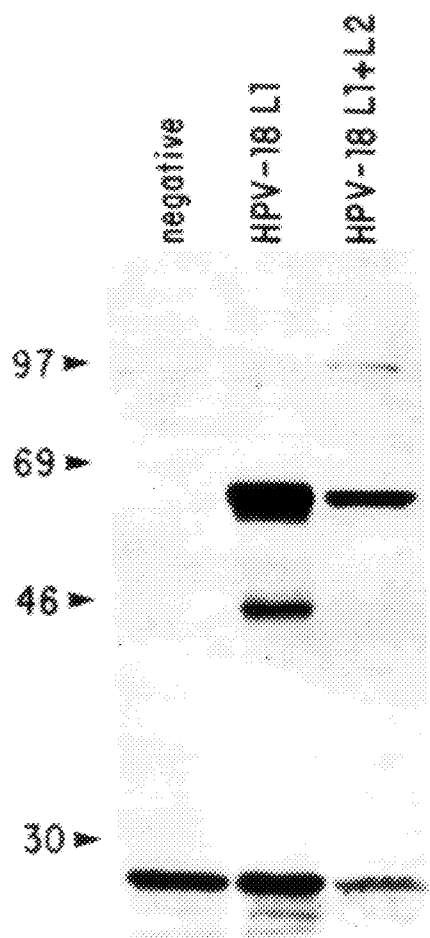
FIG. 4 shows an immunoblot of HPV 18 L1 protein expressed in yeast.

Papillomavirus (PV) infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. PV are species specific infective agents; a human papillomavirus does not infect a nonhuman animal.

Papillomaviruses may be classified into distinct groups based on the host that they infect. Human papillomaviruses (HPV) are further classified into more than 70 types based on DNA sequence homology. PV types appear to be type-specific immunogens in that a neutralizing immunity to infection by one type of papillomavirus does not confer immunity against another type of papillomavirus.

In humans, different HPV types cause distinct diseases. HPV types 1, 2, 3, 4, 7, 10 and 26–29 cause benign warts in both normal and inmunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause benign condylomata of the genital or respiratory mucosa. HPV types 16 and 18 cause epithelial dysplasia of the genital mucosa and are associated with the majority of in situ and invasive carcinomas of the cervix, vagina, vulva and anal canal.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55–60 kDa. The L2 protein is a minor capsid protein which has a predicted molecular weight of 55–60 kDa and an apparent molecular weight of 75–100 kDa as determined by polyacrylamide gel electrophoresis. Immunological data suggest that most of the L2 protein is internal to the L1 protein within the viral capsomere. The L1 ORF is highly conserved among different papillomaviruses. The L2 proteins are less conserved among different papillomaviruses.

The L1 and L2 genes have been identified as good targets for immunoprophylaxis. Studies in the cottontail rabbit papillomavirus (CRPV) and bovine papillomavirus (BPV) systems have shown that immunizations with the L1 and L2 proteins expressed in bacteria or by using vaccinia vectors protected animals from viral infection. Expression of papillomavirus L1 genes in baculovirus expression systems or using vaccinia vectors resulted in the assembly of virus-like particles (VLP) which have been used to induce high-titered virus-neutralizing antibody responses that correlate with protection from viral challenge.

Following HPV type 16, HPV 18 is the second most prevalent HPV type found in cervical carcinomas. HPV 18 was detected in 5–20% of cervical cancer biopsies collected from various parts of the world (Ikenberg, H. 1990. Human papillomavirus DNA in invasive genital carcinomas. In *Genital Papillomavirus Infections*, G. Gross et al., eds. p. 85–112). There appears to be a geographic dependence of infection with HPV 18 since tumor biopsies from African and South American women harbor HPV 18 more frequently than similar biopsies from European and North American women. The underlying reasons for these geographic differences are not known. The development of a vaccine against HPV 18 infection becomes extremely relevant since HPV 18 is also associated with more aggressively growing cancers and is rarely found in the milder precursor lesions, CIN I–II.

SUMMARY OF THE INVENTION

The present invention is directed to DNA molecules encoding purified human papillomavirus type 18 (HPV type 18; HPV 18) and uses of the DNA molecules.

DETAILED DESCRIPTION OF THE INVENTION

The present invention is directed to DNA molecules encoding purified human papillomavirus type 18 (HPV type 18; HPV 18) and derivatives thereof. Such derivatives include but are not limited to peptides and proteins encoded by the DNA, antibodies to the DNA or antibodies to the proteins encoded by the DNA, vaccines comprising the DNA or vaccines comprising proteins encoded by the DNA, immunological compositions comprising the DNA or the proteins encoded by the DNA, kits containing the DNA or RNA derived from the DNA or proteins encoded by the DNA.

Pharmaceutically useful compositions comprising the DNA or proteins encoded by the DNA may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the DNA or protein or VLP. Such compositions may contain DNA or proteins or VLP derived from more than one type of HPV.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 µg to about 1 mg.

The pharmaceutical compositions may be provided to the individual by a variety of routes such as subcutaneous, topical, oral, mucosal, intravenous and intramuscular.

The vaccines of the invention comprise DNA, RNA or proteins encoded by the DNA that contain the antigenic determinants necessary to induce the formation of neutralizing antibodies in the host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously, mucosally, intravenously or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in therapeutically effective amounts, that is, in amounts sufficient to generate a immunologically protective response. The therapeutically effective amount may vary according to the type of PV. The vaccine may be administered in single or multiple doses.

The DNA and DNA derivatives of the present invention may be used in the formulation of immunogenic compositions. Such compositions, when introduced into a suitable host, are capable of inducing an immune response in the host.

The DNA or its derivatives may be used to generate antibodies. The term "antibody" as used herein includes both polyclonal and monoclonal antibodies, as well as fragments thereof, such as, Fv, Fab and F(ab)2 fragments that are capable of binding antigen or hapten.

The DNA and DNA derivatives of the present invention may be used to serotype HPV infection and HPV screening. The DNA, recombinant proteins, VLP and antibodies lend themselves to the formulation of kits suitable for the detection and serotyping of HPV. Such a kit would comprise a compartmentalized carrier suitable to hold in close confinement at least one container. The carrier would further comprise reagents such as HPV 18 DNA, recombinant HPV protein or VLP or anti-HPV antibodies suitable for detecting a variety of HPV types. The carrier may also contain means for detection such as labeled antigen or enzyme substrates or the like.

The DNA and derived proteins therefrom are also useful as molecular weight and molecular size markers.

Because the genetic code is degenerate, more than one codon may be used to encode a particular amino acid, and therefore, the amino acid sequence can be encoded by any of a set of similar DNA oligonucleotides. Only one member of the set will be identical to the HPV 18 sequence but will be capable of hybridizing to HPV 18 DNA even in the presence of DNA oligonucleotides with mismatches under appropriate conditions. Under alternate conditions, the mismatched DNA oligonucleotides may still hybridize to the HPV 18 DNA to pennit identification and isolation of HPV 18 encoding DNA.

The purified HPV 18 DNA of the invention or fragments thereof may be used to isolate and purify homologues and fragments of HPV 18 from other sources. To accomplish this, the first HPV 18 DNA may be mixed with a sample containing DNA encoding homologues of HPV 18 under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site-directed mutagenesis.

As used herein, a "functional derivative" of HPV 18 is a compound that possesses a biological activity (either functional or structural) that is substantially similar to the biological activity of HPV 18. The term "functional derivatives" is intended to include the "fragments," "variants," "degenerate variants," "analogs" and "homologues" or to "chemical derivatives" of HPV 18. The term "fragment" is meant to refer to any polypeptide subset of HPV 18. The term "variant" is meant to refer to a molecule substantially similar in structure and function to either the entire HPV 18 molecule or to a fragment thereof. A molecule is "substantially similar" to HPV 18 if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical.

The term "analog" refers to a molecule substantially similar in function to either the entire HPV 18 molecule or to a fragment thereof.

A variety of procedures may be used to molecularly clone HPV 18 DNA. These methods include, but are not limited to, direct functional expression of the HPV 18 genes following the construction of a HPV 18-containing cDNA or genomic DNA library in an appropriate expression vector system. Another method is to screen HPV 18-containing cDNA or genomic DNA library constructed in a bacteriophage or plasmid shuttle vector with a labeled oligonucleotide probe designed from the amino acid sequence of the HPV 18. An additional method consists of screening a HPV 18-containing cDNA or genomic DNA library constructed in a bacteriophage or plasmid shuttle vector with a partial DNA encoding the HPV 18. This partial DNA is obtained by the specific polymerase chain reaction (PCR) amplification of HPV 18 DNA fragments through the design of degenerate oligonucleotide primers from the amino acid sequence of purified HPV 18. Another method is to isolate RNA from HPV 18-producing cells and translate the RNA into protein via an in vitro or an in vivo translation system. The translation of the RNA into a peptide or a protein will result in the production of at least a portion of HPV 18 protein which can be identified by, for example, the activity of HPV 18 protein or by immunological reactivity with an anti-HPV 18 antibody. In this method, pools of RNA isolated from HPV 18-producing cells can be analyzed for the presence of an RNA which encodes at least a portion of the HPV 18. Further fractionation of the RNA pool can be done to purify the HPV 18 RNA from non-HPV 18 RNA. The peptide or protein produced by this method may be analyzed to provide amino acid sequences which in turn are used to provide primers for production of HPV 18 cDNA, or the RNA used for translation can be analyzed to provide nucleotide sequences encoding HPV 18 and produce probes for the screening of a HPV 18 cDNA library. These methods are known in the art and can be found in, for example, Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

It is apparent that other types of libraries, as well as libraries constructed from other cells or cell types, may be useful for isolating HPV 18-encoding DNA. Other types of libraries include, but are not limited to, cDNA libraries derived from other cells or cell lines containing HPV type 18 and genomic DNA libraries.

Preparation of cDNA libraries can be performed by a variety of techniques. cDNA library construction techniques can be found in Sambrook, J., et al., supra. It is apparent that DNA encoding HPV 18 may also be isolated from a suitable genomic DNA library. Construction of genomic DNA libraries can be performed by a variety of techniques. Genomic DNA library construction techniques can be found in Sambrook, J., et al. supra.

The cloned HPV 18 DNA or fragments thereof obtained through the methods described herein may be recombinantly expressed by molecular cloning into an expression vector containing a suitable promoter and other appropriate transcription regulatory elements, and transferred into prokaryotic or eukaryotic host cells to produce recombinant HPV 18. Techniques for such manipulations are fully described in Sambrook, J., et al., supra, and are known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells. Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express HPV 18 DNA or fragments thereof in mammalian cells. Commercially available mammalian expression vectors which may be suitable for recombinant HPV 18 expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express HPV 18 DNA or fragments thereof in bacterial cells. Commercially available bacterial expression vectors which may be suitable include, but are not limited to pET11a (Novagen), lambda gt11 (Invitrogen), pcDNAII (Invitrogen), pKK223-3 (Pharmacia).

A variety of fungal cell expression vectors may be used to express HPV 18 or fragments thereof in fungal cells. Commercially available fungal cell expression vectors which may be suitable include but are not limited to pYES2 (Invitrogen), Pichia expression vector (Invitrogen), and Hansenula expression (Rhein Biotech, Dusseldorf, Germany).

A variety of insect cell expression vectors may be used to express HPV 18 DNA or fragments thereof in insect cells. Commercially available insect cell expression vectors which may be suitable include but are not limited to pBlue Bac III (Invitrogen) and pAcUW51 (PharMingen, Inc.).

An expression vector containing DNA encoding HPV 18 or fragments thereof may be used for expression of HPV 18 proteins or fragments of HPV 18 proteins in a cell, tissues, organs, or animals (including humans). Host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK$^-$) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce HPV 18 protein. Identification of HPV 18 expressing host cell clones may be done by several means, including but not limited to immunological reactivity with anti-HPV 18 antibodies, and the presence of host cell-associated HPV 18 activity, such as HPV 18-specific ligand binding or signal transduction defined as a response mediated by the interaction of HPV 18-specific ligands with the expressed HPV 18 proteins.

Expression of HPV DNA fragments may also be performed using in vitro produced synthetic MRNA or native MRNA. Synthetic mRNA or mRNA isolated from HPV 18 producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Following expression of HPV 18 protein(s) in a host cell, HPV 18 protein may be recovered to provide HPV 18 in purified form. Several HPV 18 purification procedures are available and suitable for use. As described herein, recombinant HPV 18 protein may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant HPV 18 may be separated from other cellular proteins by use of an immunoaffinity column made with monoclonal or polyclonal antibodies specific for full length nascent HPV 18, or polypeptide fragments of HPV 18. Monoclonal and polyclonal antibodies may be prepared according to a variety of methods known in the art. Monoclonal or monospecific antibody as used herein is defined as a single antibody species or multiple antibody species with homogenous binding characteristics for HPV 18. Homogenous binding as used herein refers to the ability of the antibody species to bind to a specific antigen or epitope.

It is apparent that the methods for producing monospecific antibodies may be utilized to produce antibodies specific for HPV 18 polypeptide fragments, or full-length nascent HPV 18 polypeptide. Specifically, it is apparent that monospecific antibodies may be generated which are specific for the fully functional HPV 18 or fragments thereof.

The present invention is also directed toward methods for screening for compounds which modulate the expression of DNA or RNA encoding HPV 18 as well as the function(s) of HPV 18 protein(s) in vivo. Compounds which modulate these activities may be DNA, RNA, peptides, proteins, or non-proteinaceous organic molecules. Compounds may modulate by increasing or attenuating the expression of DNA or RNA encoding HPV 18, or the function of HPV 18 protein. Compounds that modulate the expression of DNA or RNA encoding HPV 18 or the function of HPV 18 protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing HPV 18 DNA, fragments of HPV 18 DNA, antibodies to HPV 18 DNA or HPV 18 protein, HPV 18 RNA or HPV 18 protein may be prepared. Such kits are used to detect DNA which hybridizes to HPV 18 DNA or to detect the presence of HPV 18 protein(s) or peptide fragments in a sample. Such characterization is useful for a variety of purposes including but not limited to forensic analyses and epidemiological studies.

Nucleotide sequences that are complementary to the HPV 18 encoding DNA sequence may be synthesized for antisense therapy. These antisense molecules may be DNA, stable derivatives of DNA such as phosphorothioates or methylphosphonates, RNA, stable derivatives of RNA such as 2'-O-alkylRNA, or other HPV 18 antisense oligonucleotide mimetics. HPV 18 antisense molecules may be introduced into cells by microinjection, liposome encapsulation or by expression from vectors harboring the antisense sequence. HPV 18 antisense therapy may be particularly useful for the treatment of diseases where it is beneficial to reduce HPV 18 activity.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the HPV 18 or its activity while minimizing any potential toxicity. In addition, co-administration or sequential administration of other agents may be desirable.

Advantageously, compounds of the present invention may be administered in a single daily dose, or the total daily dosage may be administered in several divided doses. Furthermore, compounds for the present invention may be administered via a variety of routes including but not limited to intranasally, orally, transdermally or by suppository.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Cloning of HPV 18 genome

Total genomic DNA was prepared from the human cervical carcinoma-derived cell line, SW756 (Freedman, R. S., et al., 1982, In Vitro, Vol 18, pages 719–726) by standard techniques. The DNA was digested with EcoR1 and electrophoresed through a 0.8% low-melting temperature, agarose preparative gel. A gel slice was excised corresponding to DNA fragments approximately 12 kbp in length. The agarose was digested using Agarase™ enzyme (Boehringer Mannheim, Inc.) and the size-fractionated DNA was precipitated, dephosphorylated and ligated with EcoR1 digested lambda EMBL4 arms (Stratagene, Inc.). The lambda library was packaged using Gigapack II Gold packaging extract (Stratagene, Inc.). HPV 18-positive clones were identified using a 700 bp, HPV 18 L1 DNA probe that was generated by polymerase chain reaction (PCR) using SW756 DNA as template and oligonucleotide primers that were designed based on the published HPV 18 L1 DNA sequence (Cole and Danos, 1987, J. Mol. Biol., Vol. 193:599–608; Genbank Accession #X05015). A HPV 18-positive, lambda clone was isolated that contained a 12 kbp EcoR1 fragment insert and was designated as #187-1.

EXAMPLE 2

Construction of Yeast Expression Vectors

The HPV 18 L1 open reading frame (ORF) was amplified by PCR using clone #187-1 as template, Vent polymerase™ (New England Biolabs, Inc.), 10 cycles of amplification (94° C., 1 min; 50° C., 1 min; 72° C., 2 min) and the following oligonucleotide primers which contain flanking BglII sites (underlined):

sense primer, 5'-GAAGATCTCACAAAACAAAATGGCTTTGT-GGCGGCCTAGTG-3', (SEQ ID NO:5)

antisense primer, 5'-GAAGATCTTTACTTCCTGGCACGTACACGCA-CACGC-3'(SEQ ID NO:6).

The sense primer introduces a yeast non-translated leader sequence (Kniskern, et al., 1996, Gene, Vol. 46:135–141) immediately upstream to the HPV 18 L1 initiating methionine codon (highlighted in bold print). The 1.5 kbp L1 PCR product was digested with BglII and gel purified.

The pGAL1-10 yeast expression vector was constructed by isolating a 1.4 kbp SphI fragment from a pUC 18/bidirectional GAL promoter plasmid which contains the *Saccharomyces cerevisiae* divergent GAL1–GAL10 promoters from the plasmid pBM272 (provided by Mark Johnston, Washington University, St. Louis, Mo.). The divergent promoters are flanked on each side by a copy of the yeast ADH1 transcriptional terminator, a BamHI cloning site located between the GAL1 promoter and the first copy of the ADH1 transcriptional terminator and a SmaI cloning site located between the GAL10 promoter and the second copy of the ADH1 transcriptional terminator. A yeast shuttle vector consisting of pBR322, the yeast LEU2d gene, and the yeast 2μ plasmid (gift of Benjamin Hall, University of Washington, Seattle, Wash.) was digested with SphI and ligated with the 1.4 kbp SphI divergent GAL promoter fragment resulting in pGAL1-10. pGAL1-10 was linearized with BamHI which cuts between the GAL1 promoter and the ADH1 transcription terminator. The BamHI digested vector and the BglII digested HPV 18 L1 PCR fragment were ligated and used to transform *E. coli* DH5 cells (Gibco BRL, Inc.). A pGAL1-10 plasmid was isolated which contains the HPV 18 L1 gene and was designated p191-6.

A yeast expression vector that co-expresses both the HPV 18 L1 and L2 genes was constructed. Plasmid p191-6 (pGAL1-10+HPV 18 L1) was digested with SmaI which cuts between the GAL10 promoter and the ADH1 transcription terminator. The 1.4 kbp HPV 18 L2 gene was amplified by PCR as described above using the following oligonucleotide primers which contain flanking SmaI sites (underlined):

sense primer, 5'-TCCCCCGGGCACAAAACAAAATGGTATCCC-ACCGTGCCGCACGAC-3', (SEQ ID NO:7)

antisense primer, 5'-TCCCCCGGGCTAGGCCGCCACAAAGCCAT-CTGC-3'(SEQ ID NO:8).

The sense primer introduces a yeast non-translated leader sequence (Kniskern et al., 1986, supra) immediately upstream to the HPV 18 L2 initiating methionine codon (highlighted in bold print). The PCR fragment was digested with SmaI, gel purified and ligated with the SmaI digested p191-6 plasmid. A pGAL1-10 plasmid containing both the HPV 18 L1 and L2 genes was isolated and designated, p195-11.

EXAMPLE 3

Typing of Clinical Samples

Cervical biopsy samples were collected at the Veterans Administration Medical Center in Indianapolis, Ind. (courtesy of Dr. Darron Brown) and at the Albert Einstein Medical Center in Philadelphia, Pa. (courtesy of Dr. Joan Adler) and were frozen at −20° C. DNA was isolated as described by Brown et al., 1993 (Brown, D. et al., 1993, J. clin. Microbiol., Vol. 31:2667–2673). Briefly, clinical specimens were processed with a Braun mikro-dismembrator II (B. Braun Instruments, Melsungen, Germany) and solubilized in buffer containing 10 mM EDTA and 0.6% (w/v) sodium dodecyl sulfate (SDS). Samples were adjusted to 20 mM Tris pH 7.4 and protein was digested with 50 mcg/mL Proteinase K in the presence of 0.1 mcg/mL RNase A followed by extraction with phenol/chloroform/isoamyl alcohol. DNA was ethanol precipitated and quantified by spectrophotometry.

The DNA samples were screened for the presence of HPV 18 by PCR and Southern blot analyses. A 256 bp segment of the HPV 18 L1ORF was amplified by PCR using the following oligonucleotide primers:

sense primer, 5'-CAATCCTTATATATTAAAGGCACAGGTATG-3', antisense primer (SEQ ID NO:9), 5'-CATCATATTGCCCAGGTACAGGAGACTGTG-3' (SEQ ID NO:10).

The PCR conditions were according to the manufacturer's recommendations for the AmpliTaq™ DNA Polymerase/GeneAmp™ kit (Perkin Elmer Corp.) except that 0.5 µl of clinical sample DNA was used as template and 10 pmoles of each primer, 2 mM dNTPs and 2.0 mM $MgCl_2$ were in the final reaction mixture. A 2 min, 94° C. denaturation step was followed by 40 cycles of amplification (94° C., 1 min; 45° C., 1 min; 72° C., 1 min). The PCR products were electrophoresed through a 3.0% agarose gel, blotted onto nylon membranes and hybridized with a $^{32}$P-labeled HPV 18 L1-specific oligonucleotide probe.

EXAMPLE 4

DNA Sequencing of L1 and L2 genes

The HPV 18 L1 and L2 genes in clones #187-1, p191-6 and p195-11 were sequenced using the PRIZM Sequencing kit and the automated DNA ABI Sequencer #373A (Applied Biosystems). To obtain a consensus HPV 18 sequence, portions of the L1 gene DNA were amplified by PCR from human clinical isolates, sequenced and compared to the claimed and published sequences. A 256 bp fragment (nucleotides 817–1072) was amplified from each clinical DNA isolate for this purpose using the oligonucleotides and heating cycles described in Example 3. The following primers, 5'-GAAGATCTCACAAAACAAAATGGCTTTGTGG-CGGCCTAGTG-3'(SEQ ID NO:11)3' and 5'-CCTAACGTCCTCAGAAACAT-3'(SEQ ID NO:12) were used to amplify an amino-terminal 432 bp portion of L1 DNA (nucleotides 1-431) using the heating cycles described in Example 3. Both PCR products were ligated separately with plasmid pCRII (Invitrogen Corp.) using the reagents and procedures recommended by the manufacturer. Plasmid DNA was isolated from the transformants and those containing EcoRI inserts were sequenced.

EXAMPLE 5

Analysis of DNA and Deduced Amino Acid Sequences

The nucleotide and deduced amino acid (aa) sequences of the claimed HPV 18 L1 are shown in FIG. 1. The DNA sequence was derived from a consensus of clones #187-1, p191-6 and p195-11. A comparison of the claimed HPV 18 L1 nucleotide sequence with the published HPV 18 L1 sequence (Genbank Accession #X05015) identified 20 bp changes out of 1524 bps. Five of the nucleotide changes (C to G at position 89, C to A at 263, C to G at 848, G to A at 967 and C to G at 1013) result in amino acid substitutions. The five residue differences from published are P to R at aa positions 30, 283 and 338, T to N at aa 88 and V to I at aa 323 (FIG. 2). Positions 88 and 323 represent conservative changes while the three P to R changes may substantially alter the physical properties of the expressed L1 protein.

A comparison of the amino acid sequences derived from clinical isolates (numbers 354, 556, 755, 697, 795 and 23) with the claimed sequence and the published sequence is shown in FIG. 2. There are four locations where the clinical isolates and the claimed sequence differ from the published sequence. Positions 30, 283 and 338 encode arginine (R) in all the isolates found to date, including the claimed sequence. This is in sharp contrast to the published sequence which has prolines (P) at each of these locations. Furthermore, position 88 is an asparagine (N) in the isolates and the claimed sequence but is a threonine (T) in the published sequence. The last difference, position 323, was found to be a valine (V) in many of the clinical isolates and the published strain versus an isoleucine (I) in the claimed sequence and one of the isolates (#23). The conclusion is that the claimed sequence reflects the predominant viral sequences that are associated with clinical infections and the absence of isolates containing any of the position 30, 293 or 338 prolines of the published sequence suggests that the published clone is either an artefact or an inconsequential subtype.

The nucleotide and deduced aa sequences of HPV 18 L2 were derived from a consensus sequence of clones #187-1 and p195-11 and are shown in FIG. 3. A comparison of the L2 nucleotide sequence with the published HPV 18 sequence (Genbank Accession #X05015) identified 40 bp changes out of 1389 bps. The bp differences result in 14 changes at the aa level: P to S at aa 29, P to N at aa 33, A to S at aa 177, D to E at aa 266, D to N at aa 270, D to G at aa 346, M to I at 355, V to M at aa 359, S to P at aa 365, F to S at aa 369, F to V at aa 371, F to S at aa 372, K to T at aa 373 and S to P at aa 409.

EXAMPLE 6

Generation of HPV 18 L2 Antiserum

HPV 18 L2 specific antibodies were prepared in goats using a trpE-HPV 18 L2 fusion protein expressed in E. coli. The full-length L2 ORF was amplified by PCR using oligonucleotide primers providing HindIII and BamHI sites flanking the 5'- and 3'- ends, respectively. The L2 fragment was inserted into the HindIII-BamHI digested, pATH23 expression plasmid (Koerner at al., 1991, Meth. Enzymol. Vol. 194:477–490). The fusion protein was expressed in E. coli RR1 cells (Gibco BRL, Inc.) after induction with 3-b-indoleacrylic acid. The insoluble fraction was analyzed by SDS-PAGE followed by staining with Coomassie Blue. The trpE-L2 fusion protein accounted for the major portion of the E. coli insoluble fraction. Goats were immunized with the trpE-L2 fusion protein according to the standard protocol of Pocono Rabbit Farm and Laboratory, Inc. for fusion protein antigens (Protein Rabbit Farm, Canadensis, Pa.).

EXAMPLE 7

Preparation of Yeast Strain U9

Saccharomyces cerevisiae strain 2150-2-3 (MATalpha, leu2-04, adel, cir°) was obtained from Dr. Leland Hartwell (University of Washington, Seattle, Wash.). Cells of strain 2150-2-3 were propagated overnight at 30° C. in 5 mL of YEHD medium (Carty et al., J. Ind Micro 2 (1987) 117–121). The cells were washed 3 times in sterile, distilled water, resuspended in 2 mL of sterile distilled water, and 0.1 mL of cell suspension was plated onto each of six 5-fluoroorotic acid (FOA) plates in order to select for ura3 mutants (Cold Spring Harbor Laboratory Manual for Yeast Genetics). The plates were incubated at 30° C. The medium contained per 250 mL distilled water: 3.5 g, Difco Yeast Nitrogen Base without amino acids and ammonium sulfate; 0.5 g 5-Fluoro-orotic acid; 25 mg Uracil; and 10.0 g Dextrose.

The medium was sterilized by filtration through 0.2 µm membranes and then mixed with 250 mL of 4% Bacto-Agar (Difco) maintained at 50° C., 10 mL of a 1.2 mg/mL solution of adenine, and 5 mL of L-leucine solution (180 mg/50 mL). The resulting medium was dispensed at 20 mL per petri dish.

After 5 days of incubation, numerous colonies had appeared. Single colonies were isolated by restreaking colonies from the initial FOA plates onto fresh FOA plates which were then incubated at 30° C. A number of colonies from the second set of FOA plates were tested for the presence of the ura3 mutation by replica-plating onto both YEHD plates and uracil-minus plates. The desired result was good growth on YEHD and no growth on uracil-minus medium. One isolate (U9) was obtained which showed these properties. It was stored as a frozen glycerol stock (strain #325) at −70° C. for later use.

EXAMPLE 8
Preparation of a Vector for disruption of the Yeast MNN9 gene

In order to prepare a vector for disruption of the MNN9 gene, it was necessary to first clone the MNN9 gene from S. cerevisiae genomic DNA. This was accomplished by standard Polymerase Chain Reaction (PCR) technology. A 5' sense primer and 3' antisense primer for PCR of the full-length MNN9 coding sequence were designed based on the published sequence for the yeast MNN9 gene (Zymogenetics: EPO Patent Application No. 88117834.7, Publication No. 0-314-096-A2). The following oligodeoxy-nucleotide primers containing flanking HindIII sites (underlined) were used:

sense primer: 5'-CTT AAA GCT TAT GTC ACT TTC TCT TGT ATC G-3'(SEQ ID NO:13)
antisense primer: 5'-TGA TAA GCT TGC TCA ATG GTT CTC TTC CTC-3'(SEQ ID NO:14)

The initiating methionine codon for the MNN9 gene is highlighted in bold print. The PCR was conducted using genomic DNA from S. cerevisiae strain JRY188 as template, Taq DNA polymerase (Perkin Elmer) and 25 cycles of amplification (94° C. 1 min., 37° C. 2 min., 72° C. 3 min.). The resulting 1.2 kbp PCR fragment was digested with HindIII, gel-purified, and ligated with HindIII-digested, alkaline-phosphatase treated pUC13 (Pharmacia). The resulting plasmid was designated p1183.

In order to disrupt the MNN9 gene with the yeast URA3 gene, the plasmid pBR322-URA3 (which contains the 1.1 Kbp HindIII fragment encoding the S. cerevisiae URA3 gene subcloned into the HindIII site of pBR322) was digested with HindIII and the 1.1 kbp DNA fragment bearing the functional URA3 gene was gel-purified, made blunt-ended with T4 DNA polymerase, and then ligated with PmlI-digested plasmid p1183 (PmlI cuts within the MNN9 coding sequence). The resulting plasmid p1199 contains a disruption of the MNN9 gene by the functional URA3 gene.

EXAMPLE 9
Construction of U9-derivative strain 1372 containing disruption of MNN9 gene For disruption of the MNN9 gene in strain U9 (#325), 30 μg of plasmid p1199 were digested with HindIII to create a linear mnn9::URA3 disruption cassette. Cells of strain 325 were transformed with the HindIII-digested p1199 DNA by the spheroplast method (Hinnen et al., 1978, Proc. Natl. Acad. Sci. USA 75:1929–1933) and transformants were selected on a synthetic agar medium lacking uracil and containing 1.0M sorbitol. The synthetic medium contained, per liter of distilled water: Agar, 20 g; Yeast nitrogen base w/o amino acids, 6.7 g; Adenine, 0.04 g; L-tyrosine, 0.05 g; Sorbitol, 182 g; Glucose, 20 g; and Leucine Minus Solution #2, 10 ml. Leucine Minus Solution #2 contains per liter of distilled water: L-arginine, 2 g; L-histidine, 1 g; L-Leucine, 6 g; L-Isoleucine, 6 g; L-lysine, 4 g; L-methionine, 1 g; L-phenylalanine, 6 g; L-threonine, 6 g; L-tryptophan, 4 g.

The plates were incubated at 30° C. for five days at which time numerous colonies had appeared. Chromosomal DNA preparations were made from 10 colonies and then digested with EcoRI plus HindIII. The DNA digests were then evaluated by Southern blots (J. Sambrook et al., *Molecular Cloning: A Laboratory Manual*, 2nd edition, Cold Spring Harbor Laboratory Press, 1989) using the 1.2 kbp HindIII fragment bearing the MNN9 gene (isolated from plasmid p1199) as a probe. An isolate was identified (strain #1372) which showed the expected DNA band shifts on the Southern blot as well as the extreme dumpiness typically shown by mnn9 mutants.

EXAMPLE 10
Construction of a Vector for Disruption of Yeast HIS3 Gene

In order to construct a disruption cassette in which the S. cerevisiae HIS3 gene is disrupted by the URA3 gene, the plasmid YEp6 (K. Struhl et al., 1979, Proc. Natl. Acad. Sci., USA 76:1035) was digested with BamHI and the 1.7 kbp BamHI fragment bearing the HIS3 gene was gel-purified, made blunt-ended with T4 DNA polymerase, and ligated with pUC18 which had been previously digested with BamHI and treated with T4 DNA polymerase. The resulting plasmid (designated p1501 or pUC18-HIS3) was digested with NheI (which cuts in the HIS3 coding sequence), and the vector fragment was gel-purified, made blunt-ended with T4 DNA polymerase, and then treated with calf intestine alkaline phosphatase. The URA3 gene was isolated from the plasmid pBR322-URA3 by digestion with HindIII and the 1.1 kbp fragment bearing the URA3 gene was gel-purified, made blunt-ended with T4 DNA polymerase, and ligated with the above pUC18-HIS3 NheI fragment. The resulting plasmid (designated pUC18-his3::URA3 or p1505) contains a disruption cassette in which the yeast HIS3 gene is disrupted by the functional URA3 gene.

EXAMPLE 11
Construction of Vector for Disruption of Yeast PRB1 Gene by the HIS3 Gene Plasmid FP8ΔH bearing the S. cerevisiae PRB1 gene was provided by Dr. E. Jones of Carnegie-Mellon Univ. (C. M. Moehle et al., 1987, *Genetics* 115:255–263). It was digested with HindIII plus XhoI and the 3.2 kbp DNA fragment bearing the PRB1 gene was gel-purified and made blunt-ended by treatment with T4 DNA polymerase. The plasmid pUC18 was digested with BamHI, gel-purified and made blunt-ended by treatment with T4 DNA polymerase. The resulting vector fragment was ligated with the above PRB1 gene fragment to yield the plasmid pUC18-PRB1. Plasmid YEp6, which contains the HIS3 gene, was digested with BamHI. The resulting 1.7 kbp BamHI fragment bearing the functional HIS3 gene was gel-purified and then made blunt-ended by treatment with T4 DNA polymerase. Plasmid pUC18-PRB1 was digested with EcoRV plus NcoI which cut within the PRB1 coding sequence and removes the protease B active site and flanking sequence. The 5.7 kbp EcoRV-NcoI fragment bearing the residual 5' and 3'-portions of the PRB1 coding sequence in pUC18 was gel-purified, made blunt-ended by treatment with T4 DNA polymerase, dephosphorylated with calf intestine alkaline phosphatase, and ligated with the blunt-ended HIS3 fragment described above. The resulting plasmid (designated pUC18-prb1::HIS3, stock #1245) contains the functional HIS3 gene in place of the portion of the PRB1 gene which had been deleted above.

EXAMPLE 12
Construction of a U9-related Yeast Strain containing disruptions of both the MNN9 and PRB1 Genes The U9-related strain 1372 which contains a MNN9 gene disruption was described in Example 9. Clonal isolates of strain 1372 were passaged on FOA plates (as described in Example 7) to select ura3 mutants. A number of ura3 isolates of strain 1372 were obtained and one particular isolate (strain 12930-190-S1-1) was selected for subsequent disruption of the HIS3 gene. The pUC18-his3::URA3 gene disruption vector (p1505) was digested with XbaI plus EcoRI to generate a linear his3::URA3 disruption cassette and used for transformation of strain 12930-190-S1-1 by the lithium acetate method [*Methods in Enzymology*, 194:290 (1991)]. Ura+ transformants were selected on synthetic agar medium lacking uracil, restreaked for clonal isolates on the same medium, and then replica-plated onto medium lacking either uracil or histidine to screen for those isolates that were both Ura+ and His−. One isolate (strain 12930-230-1) was selected for subsequent disruption of the PRB1 gene. The PRB1 gene disruption vector (pUC18-prb1::HIS3, stock #1245) was digested with SacI plus XbaI to generate a linear prb1::HIS3 disruption cassette and used for transformation of strain 12930-230-1 by the lithium acetate method. His+ transformants were selected on agar medium lacking histidine and restreaked on the same medium for clonal isolates. Genomic DNA was prepared from a number of the resulting His+ isolates, digested with EcoRI, and then electrophoresed on 0.8% agarose gels. Southern blot analyses were then performed using a radio-labeled 617 bp probe for the PRB1 gene which had been prepared by PCR using the following oligodeoxynucleotide primers:

5' TGG TCA TCC CAA ATC TTG AAA 3'(SEQ ID NO:15)

5' CAC CGT AGT GTT TGG AAG CGA 3'(SEQ ID NO:16)

Eleven isolates were obtained which showed the expected hybridization of the probe with a 2.44 kbp prb1::HIS3 DNA fragment. This was in contrast to hybridization of the probe with the 1.59 kbp fragment for the wild-type PRB1 gene. One of these isolates containing the desired prb1::HIS3 disruption was selected for further use and was designated strain #1558.

EXAMPLE 13
Expression of HPV 18 L1 and L2 in Yeast

Plasmids p191-6 (pGAL1-10+HPV 18 L1) and p195-11 (pGAL1-10+HPV 18 L1+L2) were used to transform *S. cerevisiae* strain #1558 (MATa, leu2-04, prb1::HIS3, mnn9::URA3, adel, cir°). Clonal isolates were grown at 30° C. in YEHD medium containing 2% galactose for 88 hours. After harvesting the cells, the cell pellets were broken with glass beads and cell lysates analyzed for the expression of HPV 18 L1 and/or HPV 18 L2 protein by immunoblot analysis. Samples containing 25 μg of total cellular protein were electrophoresed through 10% Tris-Glycine gels (Novex, Inc.) under denaturing conditions and electroblotted onto nitrocellulose filters. L1 protein was immunodetected using rabbit antiserum raised against a trpE-HPV 11 L1 fusion protein as primary antibody (Brown et al., 1994, Virology 201:46–54) and horseradish peroxidase (HRP)-linked donkey anti-rabbit IgG (Amersham, Inc.) as secondary antibody. The filters were processed using the chemiluminescent "ECL" Detection Kit (Amersham, Inc.). A 50–55 KDa L1 protein band was detected in both the L1 and L1+L2 coexpressor yeast clones (strains 1725 and 1727, respectively) and not in the negative control (pGAL1-10 without L1 or L2 genes) (FIG. 4).

Figure 5:
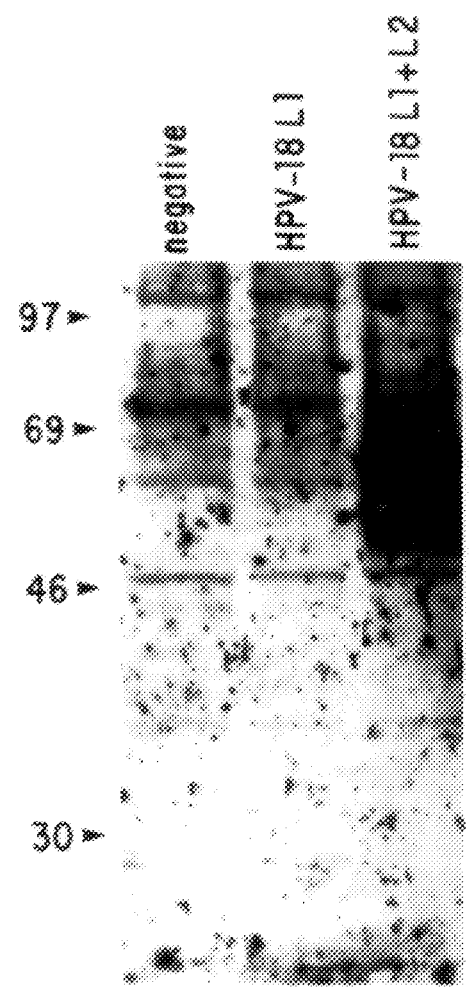
FIG. 5 shows an immunoblot of HPV 18 L2 protein expressed in yeast.

The HPV 18 L2 protein was detected by Western analysis using goat polyclonal antiserum raised against a trpE-HPV 18 L2 fusion protein as primary antibody followed by HRP-conjugated, rabbit anti-goat IgG (Kirkegaard and Perry Laboratories, Gaithersburg, Md.). The filters were processed as described above. The L2 protein was detected as a 75 kDa protein band in the L1+L2 coexpressor yeast clone (strain 1727) but not in either the negative control or the L1 expressor clone (FIG. 5).

EXAMPLE 14
Fermentation of HPV 18 L1 (strain 1725) and 18 L1+ΔL2 (strain 1727).

Surface growth of a plate culture of strains 1725 and 1727 was aseptically transferred to a leucine-free liquid medium containing (per L): 8.5 g Difco yeast nitrogen base without amino acids and ammonium sulfate; 0.2 g adenine; 0.2 g uracil; 10 g succinic acid; 5 g ammonium sulfate; 40 g glucose; 0.25 g L-tyrosine; 0.1 g L-arginine; 0.3 g L-isoleucine; 0.05 g L-methionine; 0.2 g L-tryptophan; 0.05 g L-histidine; 0.2 g L-lysine; 0.3 g L-phenylalanine; this medium was adjusted to pH 5.0–5.3 with NaOH prior to sterilization. After growth at 28° C., 250 rpm on a rotary shaker, frozen culture vials were prepared by adding sterile glycerol to a final concentration of 17% (w/v) prior to storage at −70° C. (1 mL per cryovial). Inocula were developed in the same medium (500 mL per 2-L flask) and were started by transferring the thawed contents of a frozen culture vial and incubating at 28° C., 250 rpm on a rotary shaker for 29 hr. Fermentations of each strain used a New Brunswick SF-116 fermentor with a working volume of 10 L after inoculation. The production medium contained (per L): 20 g Difco yeast extract; 10 g Sheffield HySoy peptone; 20 g glucose; 20 g galactose; 0.3 mL Union Carbide UCON LB-625 antifoam; the medium was adjusted to pH 5.3 prior to sterilization. The entire contents (500 mL) of the 2-L inoculum flask was transferred to the fermentor which was incubated at 28° C., 5 L air per min, 400 rpm, 3.5 psi pressure. Agitation was increased as needed to maintain dissolved oxygen levels of greater than 40% of saturation. Progress of the fermentation was monitored by off-line glucose measurements (Beckman Glucose 2 Analyzer) and on-line mass spectrometry (Perkin-Elmer 1200). After incubation for 66 hr, cell densities of 9.5 to 9.7 g dry cell weight per L were reached. The cultures were concentrated by hollow fiber filtration (Amicon H5MPO1-43 cartridge in an Amicon DC-10 filtration system) to ca. 2 L, diafiltered with 2 L phosphate-buffered saline, and concentrated further (to ca. 1 L) before dispensing into 500-mL centrifuge bottles. Cell pellets were collected by centrifugation at 8,000 rpm (Sorval GS-3 rotor) for 20 min at 4° C. After decanting the supernatant, the pellets (total 191 to 208 g wet cells) were stored at −70° C. until use.

EXAMPLE 15
Purification of Recombinant HPV Type 18 L1 Capsid Proteins

All steps performed at 4° C. unless noted.

Cells were stored frozen at −70° C. Frozen cells (wet weight=126 g) were thawed at 20°–23° C. and resuspended in 70 mL "Breaking Buffer" (20 mM sodium phosphate, pH 7.2, 100 mM NaCl). The protease inhibitors PMSF and pepstatin A were added to final concentrations of 2 mM and 1.7 μM, respectively. The cell slurry was broken at a pressure of approximately 16,000 psi by 4 passes in a M110-Y Microfluidizer (Microfluidics Corp., Newton, Mass.). The broken cell slurry was centrifuged at 12,000×g for 40 min to remove cellular debris. The supernatant liquid containing L1 antigen was recovered.

The supernatant liquid was diluted 1:5 by addition of Buffer A (20 mM MOPS, pH 7.0) and applied to an anion exchange capture column (9.0 cm ID×3.9 cm) of "FRAC-TOGEL" EMD TMAE-650 (M) resin (EM Separations, Gibbstown, N.J.) equilibrated in Buffer A. Following a wash with Buffer A, the antigen was eluted with a gradient of 0–1.0M NaCl in Buffer A. Column fractions were assayed for total protein by the Bradford method. Fractions were then analyzed at equal total protein loadings by Western blotting and SDS-PAGE with silver stain detection.

TMAE fractions showing comparable purity and enrichment of L1 protein were pooled. The antigen was concentrated by ammonium sulfate fractionation. The solution was adjusted to 35% saturated ammonium sulfate by adding solid reagent while gently stirring over 10 min. The sample was placed on ice and precipitation allowed to proceed for 4 hours. The sample was centrifuged at 16,000×g for 45 min. The pellet was resuspended in 20.0 mL PBS (6.25 mM Na phosphate, pH 7.2, 150 mM NaCl).

The resuspended pellet was chromatographed on a size exclusion column (2.6 cm ID×89 cm) of Sephacryl 500 HR resin (Pharmacia, Piscataway, N.J.). Running buffer was PBS. Fractions were analyzed by western blotting and SDS-PAGE with silver stain detection. The purest fractions were pooled. The resulting pool was concentrated in a 50 mL stirred cell using 43 mm YM-100 flat-sheet membranes (Amicon, Beverly, Mass.) at a $N_2$ pressure of 4–6 psi.

Final product was analyzed by western blotting and SDS-PAGE with colloidal Coomassie detection. The L1 protein was estimated to be 50–60% homogeneous. The identity of L1 protein was confirmed by western blotting. The final product was aliquoted and stored at −70° C. This process resulted in a total of 12.5 mg protein.

Bradford Assay for Total Protein

Total protein was assayed using a commercially available "COOMASSIE Plus" kit (Pierce, Rockford, Ill.). Samples were diluted to appropriate levels in Milli-Q-$H_2O$. Volumes required were 0.1 mL and 1.0 mL for the standard and microassay protocols, respectively. For both protocols, BSA (Pierce, Rockford, Ill.) was used to generate the standard curve. Assay was performed according to manufacturer's recommendations. Standard curves were plotted using "CRICKETGRAPH" software on a Macintosh IIci computer.

SDS-PAGE and Western Blot Assays

All gels, buffers, and electrophoretic apparatus were obtained from Novex (San Diego, Calif.) and were run according to manufacturer's recommendations. Briefly, samples were diluted to equal protein concentrations in Milli-Q-$H_2O$ and mixed 1:1 with sample incubation buffer containing 200 mM DTF. Samples were incubated 15 min at 100° C. and loaded onto pre-cast 12% Tris-glycine gels. The samples were electrophoresed at 125 V for 1 hr 45 min. Gels were developed using either silver staining by a variation of the method of Heukeshoven and Dernick [*Electrophoresis*, 6 (1985) 103–112] or colloidal Coomassie staining using a commercially obtained kit (Integrated Separation Systems, Natick, Mass.).

For western blots, proteins were transferred to PVDF membranes at 25 V for 40 min. Membranes were washed with Milli-Q-$H_2O$ and air-dried. Primary antibody was polyclonal rabbit antiserum raised against a TrpE-HPV 11L1 fusion protein (gift of Dr. D. Brown). Previous experiments had shown this antiserum to cross react with HPV type 18 L1 on western blots. The antibody solution was prepared by dilution of antiserum in blotting buffer (5% non-fat milk in 6.25 mM Na phosphate, pH 7.2, 150 mM NaCl, 0.02% $NaN_3$). Incubation was for at least 1 hour at 20°–23° C. The blot was washed for 1 min each in three changes of PBS (6.25 mM Na phosphate, pH 7.2, 150 mM NaCl). Secondary antibody solution was prepared by diluting goat anti-rabbit IgG alkaline phosphatase-linked conjugate antiserum (Pierce, Rockford, Ill.) in blotting buffer. Incubation proceeded under the same conditions for at least 1 hour. Blots were washed as before and detected using a 1 step NBT/BCIP substrate (Pierce, Rockford, Ill.).

EXAMPLE 16

Electron Microscopic Studies

Figure 6:
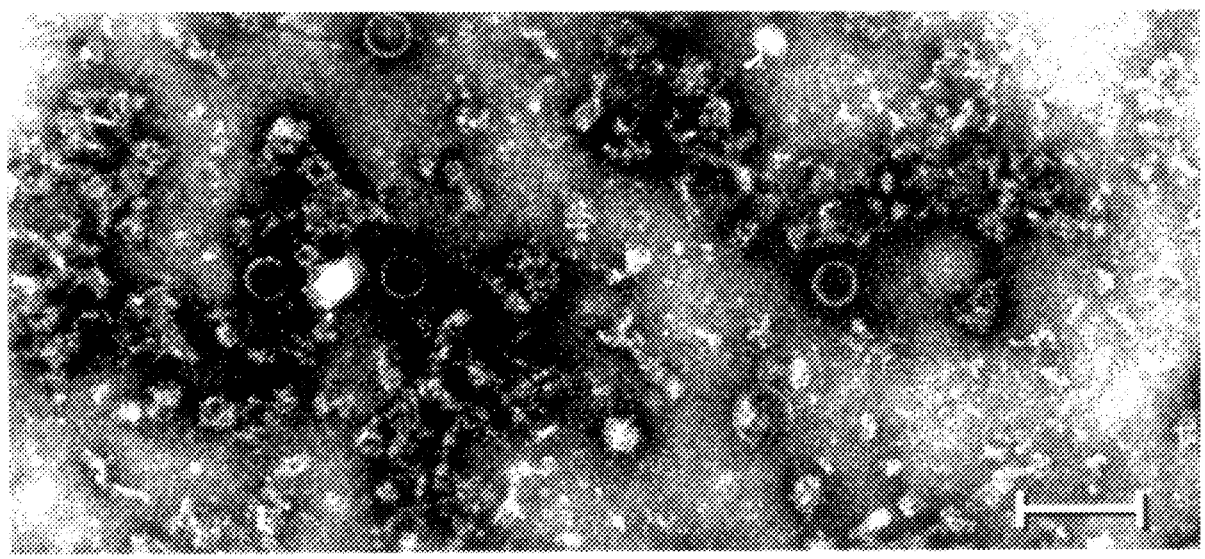
FIG. 6 is an electron micrograph of virus-like particles formed by HPV 18 L1 protein expressed in yeast.

For EM analysis (Structure Probe, West Chester, Pa.), an aliquot of each sample was placed on 200-mesh carbon-coated copper grids. A drop of 2% phosphotungstic acid (PTA), pH 7.0 was placed on the grid for 20 seconds. The grids were allowed to air dry prior to transmission EM examination. All microscopy was done using a JEOL 100CX transmission electron microscope (JEOL USA, Inc.) at an accelerating voltage of 100 kV. The micrographs generated have a final magnification of 100,000×. Virus-like particles were observed in the 50–55 nm diameter size range in the yeast sample harboring the HPV 18 L1expression plasmid (FIG. 6). No VLPs were observed in the yeast control samples.

EXAMPLE 17

Sub-cloning of the HPV 18 cDNA into expression vectors

The cDNA encoding HPV 18 is sub-cloned into several vectors for expression of the HPV 18 protein in transfected host cells and for in vitro transcription/translation. These vectors include pBluescript II SK+ (where expression is driven by T7 or T3 promoters) pcDNA I/Amp (where expression is driven by the cytomegalovirus (CMV) promoter), pSZ9016-1 (where expression is driven by the HIV long terminal repeat (LTR) promoter) and the baculovirus transfer vector pAcUW51 (PharMingen, Inc.) (where expression is driven by the polyhedrin (PH) promoter) for producing recombinant baculovirus containing the HPV 18 encoding DNA sequence.

a) pBluescript II SK+:HPV 18. The full length HPV 18 cDNA clone is retrieved from lambda bacteriophage by limited Eco RI digestion and ligated into Eco RI-cut, CIP-treated pBluescript II SK+. Separate subclones are recovered in which the sense orientation of HPV 18 followed either the T7 or T3 promoters.

b) pcDNA I/Amp:HPV 18. To facilitate directional cloning, HPV 18 is excised from a purified plasmid preparation of pBluescript II SK+:HPV 18 in which the HPV 18 DNA sequence is downstream of the T7 promoter using Esco RV and Xba I. The resulting Eco RV, Xba I HPV 18 fragment is purified and ligated into Eco RV-cut, Xba I-cut, CIP-treated pcDNA I/Amp such that the HPV 18 encoding DNA is downstream of the CMV promoter.

c) pSZ9016-1:HPV 18. HPV 18 is excised from pBluescript II SK+:HPV 18 by limited Eco RI digestion and subsequent purification of the 1.3 Kb fragment from agarose gels. The resulting Eco RI HPV 18 fragment is ligated into Eco RI-cut, CIP-treated pSZ9016-1. Subclones are selected in which the sense orientation of HPV 18 is downstream of the HIV LTR promoter.

d) pAcUW51:HPV 18 L1 The full-length HPV 18 L1 ORF was amplified by PCR from clone #187-1 using oligonucleotide primers providing flanking BglII sites. The L1 gene was inserted into the BamHI site of the baculovirus transfer vector, pAcUW51 (PharMingen, Inc.), under control of the polyhedrin promoter. Recombinant baculoviruses were generated containing the HPV 18 L1 expression cassette according to the procedures described in the Pharmingen Manual. Recombinant clones were purified by limiting dilution and dot blot hybridization.

EXAMPLE 18

Expression Of The HPV 18 Polypeptide By In Vitro Transcription/Translation And By Transfection Into Host Cells Vectors containing HPV DNA sequences are used to drive the translation of the HPV 18 polypeptide in rabbit reticulocyte lysates, mammalian host cells, and in baculovirus infected insect cells. The experimental procedures are essentially those outlined in the manufacturers' instructions.

a) In vitro Transcription/Translation. pBluescript III SK+:HPV 18 plasmid DNA (with HPV 18 in the T7 orientation) is linearized by Bam HI digestion downstream of the HPV 18 insert. The linearized plasmid is purified and used as a template for run-off transcription using T7 RNA polymerase in the presence of m7G(5')ppp(5')G. The resulting capped HPV 18 transcripts are purified by LiCl precipitation and used to drive the translation of HPV 18 in nuclease-pretreated rabbit reticulocyte lysate in the presence of L-[$^{35}$S]methionine.

b) Expression in Mammalian Cells. The HPV 18 protein is expressed in mammalian host cells following transfection with either pcDNA I/Amp:HPV 18 (under control of the CMV promoter) or pSZ9016-1:HPV 18 (under control of the HIV LTR promoter). In the latter case (pSZ9016-1:HPV 18), cells are co-transfected with the TAT expressing plasmid pSZ90161:TAT. For both HPV 18 expression plasmids, COS-7 cells are transfected using either DEAE-dextran or lipofection with Lipofectamine (BRL).

c) Expression in Insect Cells. The HPV 18 L1- containing baculovirus transfer vector pAcUW51:HPV 18 L1 is used to produce recombinant baculovirus (*Autographa californica*) by in vivo homologous recombination. Epitope tagged HPV 18 L1 is then expressed in Sf9 (*Spodoptera frugiperda*) insect cells grown in suspension culture following infection with the HPV 18 - containing recombinant baculovirus.

EXAMPLE 19

Compounds that affect HPV 18 activity may be detected by a variety of methods. A method of identifying compounds that affect HPV 18 comprises:

(a) mixing a test compound with a solution containing HPV 18 to form a mixture;

(b) measuring HPV 18 activity in the mixture; and (c) comparing the HPV 18 in the mixture to a standard.

Compounds that affect HPV 18 activity may be formulated into pharmaceutical compositions. Such pharmaceutical compositions may be useful for treating diseases or conditions that are characterized by HPV 18 infection.

EXAMPLE 20

DNA which is structurally related to DNA encoding HPV 18 is detected with a probe. A suitable probe may be derived from DNA having all or a portion of the nucleotide sequence of FIG. 1 or FIG. 3, RNA encoded by DNA having all or a portion of the nucleotide sequence of FIG. 1 or FIG. 3 or degenerate oligonucleotides derived from a portion of the sequence of FIG. 1 or FIG. 3.

What is claimed is:

1. An isolated nucleic acid encoding the amino acid sequence of FIG. 1 (SEQ ID NO:2).

2. The nucleic acid according to claim 1 which is a DNA.

3. The DNA according to claim 2 which is shown in FIG. 1 (SEQ ID NO:1).

4. A vector comprising a nucleic acid encoding the amino acid sequence of FIG. 1 (SEQ ID NO:2).

5. A cell comprising the vector of claim 4.

6. An isolated nucleic acid encoding the amino acid sequence of FIG. 3 (SEQ ID NO:4).

7. The nucleic acid according to claim 6 which is a DNA.

8. The DNA according to claim 7 which is shown in FIG. 3 (SEQ ID NO:3).

9. A vector comprising a nucleic acid encoding the amino acid sequence of FIG. 3 (SEQ ID NO:4).

10. A cell comprising the vector of claim 9.

11. A process for expressing human papilloma virus type 18 protein in a host comprising:
 (a) transforming a host cell with a vector comprising a nucleic acid encoding the amino acid sequence of SEQ ID NO:2 or SEQ ID NO:4;
 (b) culturing the host cell under conditions which allow expression of the protein from the vector.

12. A composition which induces an immune response in a subject treated with die composition, the composition comprising a nucleic acid encoding the amino acid sequence of SEQ ID NO:2 or SEQ ID NO:4 in a pharmaceutically acceptable carrier.

13. A method of inducing an immune response against an infection or disease caused by human papillomavirus 18 which comprises introducing into a susceptible animal a composition of claim 12.

* * * * *